United States Patent [19]

Berry et al.

[11] 4,014,868

[45] Mar. 29, 1977

[54] PREPARATION OF β-LACTAM ANTIBIOTICS

[75] Inventors: Antony Rodney Berry; Ian David Camburn, both of Worthing, England

[73] Assignee: Beecham Group Limited, Great Britain

[22] Filed: Sept. 2, 1975

[21] Appl. No.: 609,620

[30] Foreign Application Priority Data

Sept. 25, 1974 United Kingdom ............ 41610/74

[52] U.S. Cl. .......................... 260/239.1; 260/243 C
[51] Int. Cl.² ....................................... C07D 499/68
[58] Field of Search .................... 260/239.1, 243 C

[56] References Cited

UNITED STATES PATENTS

R28,744  3/1976  Long et al. ..................... 260/239.1

FOREIGN PATENTS OR APPLICATIONS 1,286,199  8/1972  United Kingdom ............ 260/239.1

Primary Examiner—Gerald A. Schwartz

[57] ABSTRACT

The sodium salt of amoxycillin or other β-lactam antibiotic is prepared by slurrying the antibiotic in zwitterionic form in a lower alkanol-containing organic solvent system, causing dissolution of the antibiotic by adding a sodium hydroxide or lower alkoxide, precipitating the resulting salt by adding an organic solvent and isolating the precipitate.

9 Claims, No Drawings

PREPARATION OF β-LACTAM ANTIBIOTICS

This invention relates to a method of preparing salts of β-lactam antibiotics which contain an α-amino group in the acylamino side chain.

Alkali metal salts of amphoteric β-lactam antibiotics such as ampicillin, amoxycillin, cephaloglycine and the like have often been prepared by the reaction of an alkali metal salt and an amine salt of the antibiotic in an organic solvent. This method frequently works well especially if water is excluded from the reaction system (see, for example, U.K. Pat. No. 1,286,199), but, in terms of purity of the product, considerable scope is often left for improvement in such processes. Up until the present invention, the development of improved processes has been handicapped by the necessity of using amines to help dissolve the antibiotic prior to reaction. The present invention allows the desired alkali metal salts to be prepared without first preparing an amine salt which can be beneficial in terms of yields and purity of the final product.

Accordingly, the present invention provides a process for the preparation of a sodium or potassium salt of a β-lactam antibiotic which contains an α-amino group in the acylamino side chain which process comprises (a) the formation of a slurry of the zwitterionic form of the antibiotic in an organic solvent system which contains at least one lower alkanol; (b) bringing about the dissolution of the antibiotic by the addition of a sodium or potassium hydroxide or lower alkoxide; (c) precipitating the resulting salt from solution by the addition of an organic solvent and (d) isolating the precipitate.

This reaction sequence may be applied to semi-synthetic penicillins or cephalosporins containing a group of the formula:

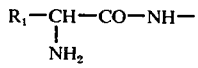

at the 6-position of the penicillin ring or 7-position of the cephalosporin ring; wherein $R_1$ is a phenyl, cyclohexadienyl, thienyl or p-hydroxyphenyl group. Thus, suitable antibiotics for use in the process of this invention include ampicillin, amoxycillin, cephaloglycine, cephradin, cephalexin and the like. This reaction sequence may prove particularly suitable for the preparation of β-lactam antibiotics wherein $R_1$ is a hydroxyphenyl group.

The process of this invention is particularly suitable for the preparation of the sodium or potassium salts of amoxycillin. Amoxycillin salts prepared by the process of this invention can be of higher purity than those produced by conventional procedures.

When used herein, the term 'lower' means that the group contains less than nine carbon atoms and more suitably less than six carbon atoms.

The solvent system used in step (a) of the reaction sequence previously described should contain 10 – 70% v/v of lower alkanol, more suitably 25 – 60% v/v of alkanol and should preferably, contain 30 – 50% v/v of alkanol. Suitable alkanols include methanol, ethanol, n-propanol, iso-propanol and the butanols. Particularly suitable alkanols include methanol, ethanol and n-propanol. Mixtures of alkanols may be used but in general such mixtures are not preferred. In addition to its alkanolic component, this solvent system will contain one or more solvents selected from conventional inert organic solvents such as the hydrocarbon, chlorinated hydrocarbon, ketonic or like solvents. The solvents may be mixed as described provided that the final system contains at least 10% alkanol and has a dielectric of at least 8 and more suitably at least 12. A preferred solvent system is a mixture of dichloromethane and methanol, especially when the methanol is present in the proportions indicated above.

For step (a), the concentration of antibiotic in the slurry is generally, 5 – 20% w/v, more suitably 8 – 15% w/v for example, about 10 or 12% w/v.

For step (b), the base used is most suitably a sodium or potassium lower alkoxide such as methoxide, ethoxide, isopropoxide or the like. Normally, the alkoxide used will be a derivative of an alkanol used in the solvent in step (a). The base to be added to the slurry is normally suspended or dissolved in an inert organic solvent system such as a chlorinated hydrocarbon optionally together with an alkanol. Preferred bases include sodium methoxide and potassium methoxide.

The temperature at which step (b) is prepared will be below 25° C, should be below 15° C, will suitably be below 0° C and will preferably be below −10° C, for example, at about −20° C to −25° C.

The molar ratio of antibiotic present to base should not be less than 0.9 to 1 and should not be greater than 1 to 1.1. Most suitably, the base is not present in excess.

For step (c), the solvent added to the solution (or vice versa), should be such that the ability of the system to form hydrogen bonds is reduced by the addition of the solvent. In general, this can occur when the solvent added is of lower dielectric constant than the existing solution. Suitable solvents include inert organic solvents such as hydrocarbons, chlorinated hydrocarbons, ketones (other than acetone), lower alkanols and the like or mixtures of such solvents.

It will be understood that neat alkanols do not form suitable solvents for this step unless the alkanol used in steps (a) and (b) is methanol or ethanol and a propanol or higher alkanol is used in step (c); even in such a case it is preferred that any alkanol added will be in admixture with at least one non-hydrogen bonding solvent.

The temperature at which step (c) is operated will normally be a depressed temperature, for example, below 15° C, suitably below 5° C and preferably below 0° C, for example at about −5° C.

The isolation of the precipitate in step (d) may be by any convenient method but in general, filtration is preferred because of ease of application. The product may be dried by known methods conventionally used in the isolation of the relevant semi-synthetic antibiotics, for example, by the passage of a stream of dry air.

In general, it is preferable that steps (a), (b) and (c) do not take place in the presence of considerable quantities of water. It is believed that the best results occur when dry reagents are used, for example, if the solvents contain less than 0.2% of water. Such conditions may be achieved by using dry materials and/or by including desiccants in the reaction system. Suitable desiccants include such conventional materials as molecular sieve, magnesium sulphate and other inorganic salts known for this purpose. Standard moisture excluding techniques may prove advantageous if used.

In order to obtain pure products, step (c) should be carried out under substantially water-free conditions.

Suitable non-alkanolic solvents for use in various stages of the process include dichloromethane, chloroform, ethylenedichloride, $C_{6-18}$ alkanes or alkenes, methylethylketone, methylisobutylketone, methyl acetate, ethyl acetate, and the like.

A preferred non-alkanolic solvent for use in the various stages of the process is dichloromethane.

A process for the preparation of the sodium or potassium salt of amoxycillin preferably comprises (a) the formation of a slurry of amoxycillin in a mixture of dichloromethane and methanol; (b) bringing about the dissolution of the amoxycillin by the addition of sodium methoxide or potassium methoxide at a temperature below 0° C; (c) precipitating the resulting salt by the addition of an organic solvent; (d) isolating the precipitated sodium or potassium salt of amoxycillin.

Most suitably stage (b) is carried out at a temperature below −10° C, for example at about −20° C to −25° C.

Most suitably the solvent added in stage (c) dichloromethane.

It is highly preferable that each of the aspects of this invention are adapted for the preparation of the sodium salt of amoxycillin.

The following Examples illustrate the invention.

EXAMPLE 1

SODIUM AMOXYCILLIN

Dry amoxycillin (45 g; containing approx. 4.5 − 5% water) was slowly added with stirring to a mixture of methanol (200 ml, water content <0.1%) and methylene dichloride (300 ml, water content <0.2%). To the resulting slurry was added Molecular Sieve grade 3A (20 − 25 ml). The slurry was cooled to −20°/25° C and a solution of sodium methoxide (5.0 g) in a mixture of methylene dichloride (100 ml, water content <0.2%) and methanol (25 ml, water content <0.1%) was added dropwise to the slurry over 20 minutes during which time the temperature was allowed to rise to −10°/15° C. The resulting solution was filtered to remove insoluble materials and poured slowly (over 1 − 2 minutes) into rapidly stirred mixture of methylene dichloride (1800 ml, water content <0.2%) and isopropanol (200 ml, water content <0.2%) pre-cooled to −5°/10° C. The resulting suspension was stirred at this temperature for 30 minutes and filtered under dry nitrogen. The resulting material was dried using a fluidised bed dryer with a dry nitrogen supply at 15°/20° C for 30 minutes and was thereafter stored in a vacuum oven at 15°/20° C for 15 hours. The resulting sodium amoxycillin was of good purity.

EXAMPLE 2

SODIUM AMOXYCILLIN

Dry amoxycillin (45 g; containing 4 − 5% water) was slurried in 200 mls of methylene dichloride (water <0.2%) and 200 mls of methanol (water <0.1%) mixture which was then cooled to −25°/−30° C. Then a solution of 5.8 g of sodium methoxide in a mixture of 225 mls methylene dichloride and 25 mls methanol was added dropwise over 30 minutes, whilst the temperature was maintained at −25°/−30 C. After a further 15 − 30 minutes the undissolved solids were removed by filtration. The resulting solution was added to 250 mls of propan-2-ol and then 2 liters of methylene dichloride (water <0.2%) was added over 15 −30 minutes whilst keeping the temperature below −5° C. The suspension was stirred for 30 minutes before being isolated by centrifuging under a dry atmosphere. The wet cake was milled, then dried at 85° C for 1 hour in a fluid-bed drier.

EXAMPLE 3

SODIUM AMOXYCILLIN

Amoxycillin trihydrate (50 g; containing 12 − 14% water) was reslurried, twice in 500 mls of methanol. The solids were isolated by filtration and the wet cake weighed. The wet cake was added to 200 mls of methylene dichloride (water <0.2%) and methanol (260 - weight of wet cake/0.8 mls) and the slurry cooled to −25°/−30° C. A solution of sodium methoxide (5.8 g) in a mixture of 225 mls of methylene dichloride and 25 mls of methanol was added slowly over 30 minutes whilst maintaining the temperature at −25°/−30° C. After a further 15 − 30 minutes, the undissolved solids were removed by filtration and the solution added to 250 mls of propan-2-ol. This mixture was diluted with 2 liters of methylene dichloride over 15 − 30 minutes, keeping the temperature below −5° C. The slurry was stirred for a further 15 − 30 minutes, then the solids were isolated by centrifuging under a dry atmosphere. The wet cake was milled, then dried at 85° C for 1 hour in a fluid-bed drier.

EXAMPLE 4

SODIUM AMOXYCILLIN

The same process as used in Example 3 was followed, except 5 − 10 minutes prior to recovering the solids by centrifuging finely ground anhydrous sodium carbonate (2.3 g) was added to the slurry.

What we claim is:

1. A process for the preparation of the sodium salt of amoxycillin which consists essentially of (a) forming a slurry of amoxycillin in a mixture of dichloromethane and methanol; (b) bringing about the dissolution of the amoxycillin by the addition of sodium methoxide at a temperature below 0° C; (c) precipitating the resulting salt by the addition of an organic solvent; and (d) isolating the precipitated sodium salt of amoxycillin.

2. A process for the preparation of the sodium salt of amoxycillin according to claim 1 wherein the solvents contain less than 0.2% water.

3. A process as claimed in claim 1 in which stage (b) is carried out at a temperature below −10° C.

4. A process as claimed in claim 3 wherein the temperature is −20° C to −25° C.

5. A process as claimed in claim 1 wherein the organic solvent added in stage (c) is dichloromethane.

6. A process for the preparation of sodium amoxycillin which consists essentially of (a) forming a slurry of zwitterionic amoxycillin in an organic solvent system which contains an alkanol of 1–4 carbon atoms; (b) bringing about the dissolution of the amoxycillin by the addition of a sodium alkoxide of 1–4 carbon atoms; (c) precipitating the resulting sodium amoxycillin from solution by the addition of an organic solvent; and (d) isolating the precipitate.

7. A process according to claim 6 wherein the lower alkanol in stage (a) is methanol, ethanol or isopropanol.

8. A process according to claim 6 wherein the lower alkanol in stage (a) is methanol and the dissolution in stage (b) is brought about by the addition of sodium methoxide.

9. A process according to claim 6 wherein the organic solvent used in stage (c) is methylene dichloride.

* * * * *